(12) United States Patent
Berka et al.

(10) Patent No.: US 6,592,929 B1
(45) Date of Patent: Jul. 15, 2003

(54) METHOD OF EXPOSING AND DEVELOPING A FINGERPRINT FROM THE SURFACE OF AN OXIDIZED METAL OBJECT

(76) Inventors: Ladislav H. Berka, 14 Walbridge Rd., Paxton, MA (US) 01612; Brian D. Elolampi, 13 Cedar Rd., Holden, MA (US) 01520

(*) Notice: Subject to any disclaimer, the term of this patent is extended or adjusted under 35 U.S.C. 154(b) by 0 days.

(21) Appl. No.: 09/939,528

(22) Filed: Aug. 24, 2001

Related U.S. Application Data

(63) Continuation of application No. 09/918,298, filed on Jul. 30, 2001, now abandoned, which is a continuation of application No. 09/878,731, filed on Jun. 11, 2001, now abandoned.
(60) Provisional application No. 60/218,369, filed on Jul. 13, 2000.

(51) Int. Cl.$^7$ ................................................ A61B 5/117
(52) U.S. Cl. ........................... 427/1; 427/336; 427/337; 427/343; 427/353; 427/354
(58) Field of Search ........................... 427/1, 336, 337, 427/343, 354, 353

(56) References Cited

U.S. PATENT DOCUMENTS

| | | | | |
|---|---|---|---|---|
| 4,529,450 A | * | 7/1985 | Panayappan | ................... 134/4 |
| 5,653,917 A | * | 8/1997 | Singerman | ............. 252/389.62 |

* cited by examiner

*Primary Examiner*—Shrive P. Beck
*Assistant Examiner*—Kirsten Crockford Jolley
(74) *Attorney, Agent, or Firm*—Blodgett & Blodgett, P.C.

(57) ABSTRACT

A method is used to expose a fingerprint on the surface of a metallic object which is covered with a layer of a metallic oxide such as rust. The metallic oxide is dissolved with a reagent which reacts with the metallic oxide. The dissolved metallic oxide is removed from the surface of the metallic object by washing with water to expose the fingerprint and a permanent copy is made of the fingerprint. More specifically, rust from a ferrous object is dissolved with an aqueous acid, the acid and dissolved rust is washed away with water, and a photograph is taken of the exposed fingerprint. The rust can also be dissolved by spraying the rust with a Precision Brand Step #3 Aerosol Rust Inhibitor and Lubricant. The rust can be removed by contacting the rust with a reagent containing a complexing agent for Fe(III) ions.

18 Claims, 1 Drawing Sheet

METHOD OF EXPOSING AND DEVELOPING A FINGERPRINT FROM THE SURFACE OF AN OXIDIZED METAL OBJECT

CROSS-REFERENCE TO RELATED APPLICATIONS

This application claims the benefit under 35 U.S.C. §119(e) of prior U.S. Provisional Application No. 60/218,369 filed Jul. 13, 2000; and is a continuation under 35 U.S.C. §120 of prior U.S. patent application Ser. No. 09/878,731, filed on Jun. 11, 2001 now abandoned; and under 35 U.S.C §120 of prior U.S. patent application Ser. No. 09/918,298, filed on Jul. 30, 2001 now abandoned; which are hereby incorporated by reference.

STATEMENT REGARDING FEDERALLY SPONSORED RESEARCH OR DEVELOPMENT

This invention has been created without the sponsorship or funding of any federally sponsored research or development program.

BACKGROUND OF THE INVENTION

The present invention relates generally to a method of exposing and developing a fingerprint from the oxidized surface of an oxidizable metallic object and, specifically, to a method of exposing and developing a fingerprint from the rusted surface of a ferrous object.

Obtaining fingerprints from a smooth object is a well developed art in forensic science. When a person touches an object with the ends of his or her fingers, a discernable "print" of the pattern of ridge lines on the person's finger is left on the object. The tips of a person's fingers contain perspiration from pores on the ridges and oils obtained from oily areas of the body such as the face. The grooves between the ridges have no pores. When a person touches an object, the sweat and oils at the ridges of the fingertips are deposited on the surface of the object in a pattern that is identical to the pattern of ridges. The sweat, which is 98% water (at least for eccrine type secretions), evaporates and the oil and sweat residue remains on the surface of the object.

When a metallic object is exposed to the elements, it oxidizes. In the case of a ferrous object, oxidization is in the form of rust. Rust is considered a hydrated iron(III) oxide of variable composition, $Fe_2O_3 \cdot nH_2O$. The number of water molecules, n, associated with each $Fe_2O_3$ unit is variable. Since the grooves between the ridges do not deposit sweat and oil on a metallic object when it is touched, rust, in the case of a ferrous object, can start forming in the spaces between the ridge lines of a fingerprint and, eventually, bridge over the ridge lines.

When an oxidizable metallic object has been exposed to the elements for a sufficient length of time, an oxide, such as rust in the case of a ferrous object, covers the surface of the object. When this occurs, any fingerprints left on the surface of the object can no longer be seen or transferred to another planar surface by conventional methods for identification. At the present time, rust is removed from firearms in forensic laboratories by using ultrasonic cleaners in order to expose serial numbers. Solvents, which are also used with this method, are highly caustic, and destroy any fingerprints which are on the firearm. These and other difficulties experienced with identifying fingerprints on the oxidized surfaces of objects have been obviated by the present invention.

It is, therefore, a principal object of the present invention to provide a method of exposing a fingerprint on the surface of an object that has become oxidized, the exposure being sufficient so that the fingerprint can be identified.

A further object of the present invention is the provision of a method of producing a copy of a fingerprint which has been exposed on the oxidized surface of an object that has been oxidized.

With these and other objects in view, as will be apparent to those skilled in the art, the invention resides in the combination of parts set forth in the specification and covered by the art, the invention resides in the combination of parts set forth in the specification and covered by the claims appended thereto.

BRIEF SUMMARY OF THE INVENTION

This invention is a method of exposing a fingerprint on the surface of a metallic object which is covered with a layer of a metallic oxide such as rust. The metallic oxide is dissolved with a reagent which reacts with the metallic oxide. The dissolved metallic oxide is removed from the surface of the metallic object by washing with water to expose the fingerprint and a permanent copy is made of the fingerprint. More specifically, rust from a ferrous object is dissolved with an aqueous acid, the acid and dissolved rust is washed away with water and a photograph is taken of the exposed fingerprint. The rust can also be dissolved by treating the rust with a reagent containing an iron complexing anion or by spraying the rust with a Precision Brand Step #3 Aerosol Rust Inhibitor and Lubricant.

BRIEF DESCRIPTION OF THE DRAWINGS

The single FIGURE is a photocopy of an enlarged photograph of a fingerprint which has been exposed on the surface of a ferrous object in accordance with the method of the present invention.

DETAILED DESCRIPTION OF THE INVENTION

Figure 1:
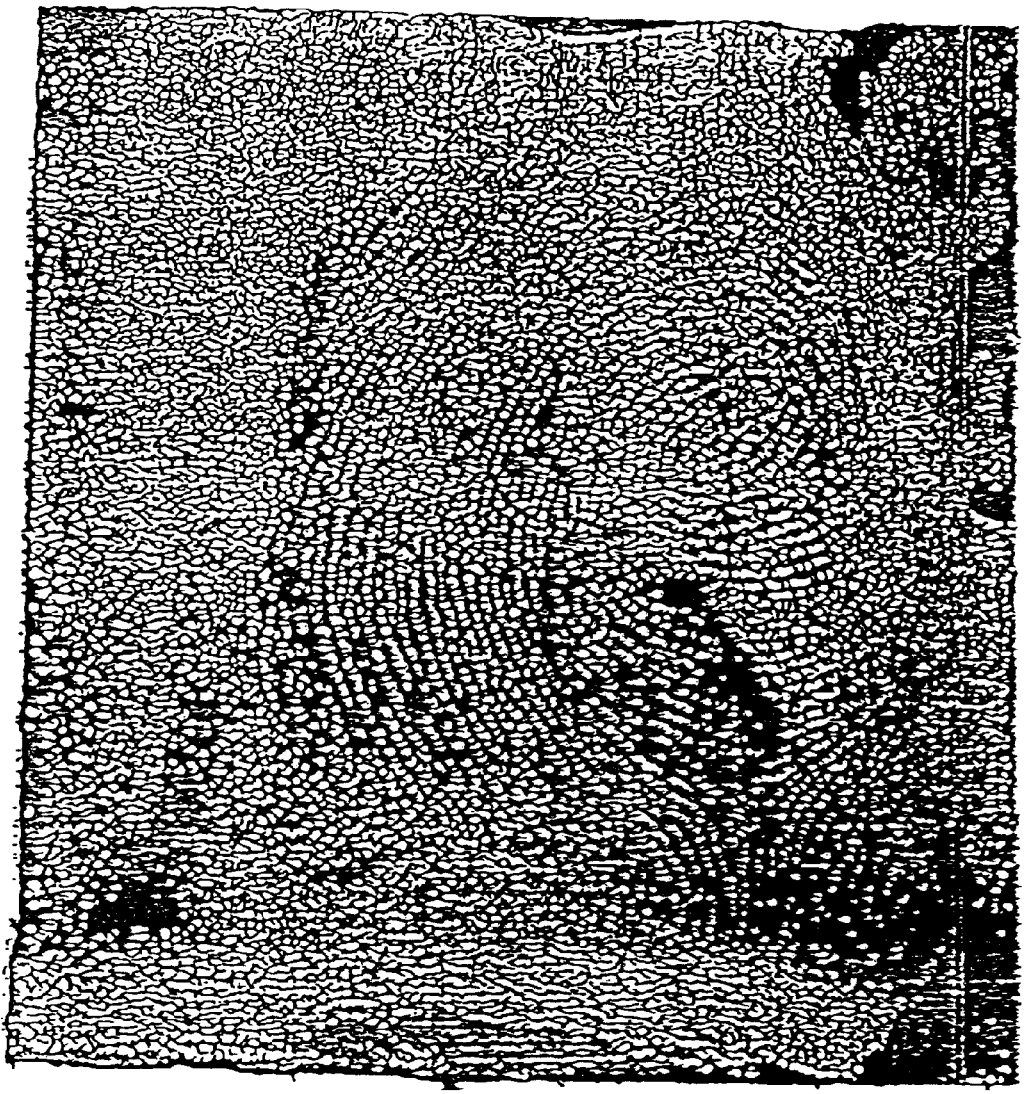

At present, three methods have been developed by us for exposing fingerprints on metal objects that are covered with rust. All three methods reveal the fingerprints in a way that the ridge details are present to such an extent that the fingerprints are identifiable for legal purposes (see FIG. 1). These methods involve removing the rust by spraying the rusted area with: 1) Precision Brand Step #3 Aerosol Rust Inhibitor and Lubricant (contains mineral spirits, propane, isobutane, heavy petroleum oxygenates, mineral oil, and propylene glycol monomethyl ether) made by Precision Brand Products, Inc., Downers Grove, Ill., or 2) a dilute solution of nitric acid, or (3) a solution of oxalic acid.

Dilute solutions of the acids; oxalic, hydrochloric, and sulfuric, have shown promise in removing the rust in a similar manner.

Other reagents which can be used for dissolving rust include: commercial rust removers (such as a naval jelly), other dilute acids (such as hydrobromic), and common household products containing acids (such as Coca-cola containing phosphoric acid).

Dissolving of Rust by Aqueous Acids

Any reagent which reacts with the Fe(III) ions or oxide ions ($O^{2-}$) has the potential of dissolving rust.

For example, a dilute aqueous solution of nitric acid is completely ionized and contains hydrogen ions, $H^+$ and nitrate ions ($NO_3^-$) produced by reaction (1):

$$HNO_3(aq) \rightarrow H^+(aq) + NO_3^-(aq) \qquad (1)$$

The hydrogen ions have a strong affinity for oxide ions to form water. This causes the rust to dissolve according to reaction (2):

$$Fe_2O_3 \cdot nH_2O(s) + 6H^+(aq) \rightarrow 2\,Fe^{3+}(aq) + (n+3)H_2O \quad (2)$$

On the other hand, oxalic acid is a weak acid which means that most of the acid in aqueous solution is only slightly ionized. However, an aqueous solution of oxalic acid has the following equilibria, with very small amounts of the products shown in reactions (3) and (4) present in the initial solution:

$$H_2C_2O_4(aq) = H^+(aq) + HC_2O_4^-(aq) \quad (3)$$

$$HC_2O_4^-(aq) = H^+(aq) + C_2O_4^{2-}(aq) \quad (4)$$

Just as hydrogen ions have a strong affinity for the oxide ions in rust, the oxalate ion $(C_2O_4)^{2-}$ has a strong affinity for Fe(III) ions, forming the complex ion, $Fe(C_2O_4)_3^{3-}$. Thus, with oxalic acid in aqueous solution, reaction (5) also occurs to dissolve the rust, along with reaction (2):

$$Fe_2O_3 \cdot nH_2O(s) + 6H^+(aq) + 3C_2O_4^{2-}(aq) \rightarrow Fe(C_2O_4)_3^{3-}(aq) + (n+3)H_2O \quad (5)$$

As reactions (2) and (5) proceed, reactions (3) and (4) occur to the right, liberating additional $H^+$ and $C_2O_4^{2-}$ ions to dissolve the remaining rust.

L-ascorbic and citric acids may dissolve rust in a manner similar to oxalic acid. The ascorbate and citrate ions may readily form complexes with Fe(III) ions.

Removal of Rust by Precision Brand Step #3 Aerosol Rust Inhibitor and Lubricant

There are at least two possible mechanisms by which this product can remove rust.

1. The heavy petroleum oxygenates and propylene glycol monomethyl ether may serve to complex the Fe(III) similar to oxalate ion [Fe(III) has a special affinity for complexing species containing oxygen atoms.]
2. Some components of the product may penetrate the rust, then provide a lubricated or greasy, reduced-friction surface which allows the rust to be removed by additional spraying of the aerosol. (The purpose of the propane and isobutane ingredients is simply to provide the spraying capability of the product and probably are not involved in removal of the rust.)

Development of the Fingerprints

No method is needed to develop the fingerprints. Once the rust is removed, the prints are starkly visible in black on the lighter metal surface. The black color may be associated with reaction products formed between the iron and the chemicals deposited in the fingerprint.

Preservation of the Fingerprints

Once the rust is removed using the chemical reagents above, the fingerprint area is immediately washed with water to remove any acid present so that it does not attack the newly exposed fingerprint. The metal surface containing the fingerprint is allowed to dry and photos are taken of the fingerprints for documentation before the iron substrate begins to rust again.

Fingerprints can be formed from deposition of eccrine secretions from glands, e.g., on the fingertips and palms of the hands, sebaceous secretions from glands, e.g., on the side of one's nose and forehead, and apocrine secretions from glands, e.g., present in underarms and/or the groin area. One eccrine component, uric acid, is not soluble in acids. Of the sebaceous components, the higher molecular weight alcohols and fatty acids are also not soluble in acids, as are glycerides and saturated hydrocarbons. Higher molecular weight carbohydrates, proteins, and sterols that are included among the apocrine secretions are also insoluble in acids.

In the case of the aerosol product, it contains mineral oil which could cover the metal surface containing the fingerprint and protect it from attack by other ingredients in the aerosol or by renewed air oxidation.

What is claimed is:

1. A method of exposing and developing a fingerprint on the surface of a metallic object which surface is covered with a layer of metallic oxide, said method comprising the following steps:

(a) applying a mixture to said layer of metallic oxide to dissolve said metallic oxide;

(b) removing said dissolved metallic oxide from said surface to expose said fingerprint; and (c) making a permanent copy of said fingerprint.

2. The method as recited in claim 1, wherein said object is a ferrous metal, said layer is hydrated ferric oxide and said mixture is nitric acid.

3. The method as recited in claim 1, wherein said object is a ferrous metal, said layer is hydrated ferric oxide and said mixture is oxalic acid.

4. The method as recited in claim 1, wherein said object is a ferrous metal, said is layer is hydrated ferric oxide and said mixture is L-ascorbic acid.

5. The method as recited in claim 1, wherein said object is a ferrous metal, said layer is hydrated ferric oxide and said mixture is citric acid.

6. The method as recited in claim 1, wherein said mixture is propylene glycol monomethyl ether and heavy petroleum oxygenates.

7. The method as recited in claim 6, wherein propylene glycol monomethyl ether is delivered to said layer by an aerosol spray.

8. The method as recited in claim 7, wherein said dissolved metallic oxide is removed from surface by an additional aerosol spray of said propylene glycol monomethyl ether and heavy petroleum oxygenates and said surface is washed with water.

9. The method as recited in claim 1, wherein said dissolved metallic oxide is removed from said surface with water.

10. The method as recited in claim 9, wherein said permanent copy of said fingerprint is made by taking a photograph of said print after said surface has been washed with water and allowed to dry.

11. The method as recited in claim 1, wherein said permanent copy of said fingerprint is made by taking a photograph of said fingerprint.

12. A method as recited in claim 1, wherein the mixture is acidic.

13. A method of exposing and developing a fingerprint on the surface of a ferrous object which surface is covered with a layer of hydrated ferric oxide, said method comprising the following step:

(a) applying a reagent which reacts with the ferric ions or oxide ions of the hydrated ferric oxide, said applying being done in a manner that effectively exposes and develops the fingerprint on the surface of a ferrous object.

14. The method as recited in claim 13, wherein said reagent is an aerosol rust inhibitor and lubricant spray containing mineral spirits, propane, isobutane, heavy petroleum oxygenates, mineral oil, and propylene glycol monomethyl ether.

15. The method as recited in claim 13, wherein the developed fingerprint is preserved.

16. The method as recited in claim 13, wherein a visual facsimile of the developed fingerprint is preserved.

17. The method as recited in claim 13, wherein the evidentiary value of the developed fingerprint is preserved.

18. A method of exposing and developing a fingerprint on the surface of a ferrous object which surface is covered with a layer of hydrated ferric oxide, said method comprising the following step:

(a) applying a reagent which reacts with the ferric ions or oxide ions of the hydrated ferric oxide to dissolve said hydrated ferric oxide, wherein said reagent is an aerosol rust inhibitor and lubricant spray containing mineral spirits, propane, isobutane, heavy petroleum oxygenates, mineral oil, and propylene glycol monomethyl ether.

* * * * *